United States Patent
Evans et al.

(10) Patent No.: US 8,062,868 B2
(45) Date of Patent: Nov. 22, 2011

(54) METHOD OF FORMING AN ELECTRICALLY CONDUCTIVE CELLULOSE COMPOSITE

(75) Inventors: Barbara R. Evans, Oak Ridge, TN (US); Hugh M. O'Neill, Knoxville, TN (US); Jonathan Woodward, Ashtead (GB)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 12/728,594

(22) Filed: Mar. 22, 2010

(65) Prior Publication Data

US 2010/0176350 A1   Jul. 15, 2010

Related U.S. Application Data

(62) Division of application No. 11/153,146, filed on Jun. 15, 2005, now Pat. No. 7,709,133.

(51) Int. Cl.
   *C12P 19/00* (2006.01)
(52) U.S. Cl. .......................................... 435/72; 435/170
(58) Field of Classification Search .................. 435/170, 435/72
   See application file for complete search history.

(56) References Cited

U.S. PATENT DOCUMENTS

| | | | | |
|---|---|---|---|---|
| 3,615,829 A | * | 10/1971 | Sprague | 429/103 |
| 4,670,300 A | * | 6/1987 | Stewart, Jr. | 427/115 |
| 5,382,405 A | * | 1/1995 | Lowrance et al. | 505/125 |
| 5,955,326 A | | 9/1999 | Bungay, III et al. | |
| 2003/0113610 A1 | | 6/2003 | Evans et al. | |
| 2003/0118904 A1 | | 6/2003 | Hosokawa et al. | |
| 2005/0079386 A1 | | 4/2005 | Brown, Jr. et al. | |
| 2006/0068667 A1 | | 3/2006 | Zabetakis et al. | |
| 2008/0297878 A1 | | 12/2008 | Brown et al. | |

OTHER PUBLICATIONS

Yoshino, K. et al. "Electrical property of pyrolzed bacterial cellulose and its intercalation effect", 1991, Synthetic Metals 41-43, 153-1596—Abstract.
Shah, J. et al. "Towards electronic paper displays made from microbial cellulose", 2005, Appl Microbiol Biotechnol, 66:352-355.
Serafica, G. et al. "Inclusion of solid particles in bacterial cellulose", 2002, Appl Microbiol Biotechnol, 58:756-760.
Evans, B. et al. "Palladium-bacteria cellulose membranes for fuel cells", 2003, Biosensors and Bioelectronics, 18:917-923.

* cited by examiner

*Primary Examiner* — Allison M. Ford
*Assistant Examiner* — Susan E Fernandez
(74) *Attorney, Agent, or Firm* — Novak Druce + Quigg LLP

(57) ABSTRACT

An electrically conductive cellulose composite includes a cellulose matrix and an electrically conductive carbonaceous material incorporated into the cellulose matrix. The electrical conductivity of the cellulose composite is at least 10 μS/cm at 25° C. The composite can be made by incorporating the electrically conductive carbonaceous material into a culture medium with a cellulose-producing organism, such as *Gluconoacetobacter hansenii*. The composites can be used to form electrodes, such as for use in membrane electrode assemblies for fuel cells.

7 Claims, 3 Drawing Sheets

METHOD OF FORMING AN ELECTRICALLY CONDUCTIVE CELLULOSE COMPOSITE

CROSS-REFERENCE TO RELATED APPLICATIONS

This application is a divisional application of U.S. application Ser. No. 11/153,146, filed Jun. 15, 2005 now U.S. Pat. No. 7,709,133, the entirety of which is incorporated herein by reference. Applicants claim the benefit of this prior patent application.

STATEMENT REGARDING FEDERALLY SPONSORED RESEARCH OR DEVELOPMENT

The United States Government has certain rights to this invention pursuant to Contract No. DE-AC05-00OR22725 between the United States Department of Energy and UT-Battelle, LLC.

FIELD OF THE INVENTION

This invention relates generally to cellulose composites, and more particularly to electrically conductive cellulose composites, and methods of making such composites.

BACKGROUND OF THE INVENTION

Cellulose is the most abundant biologically synthesized polymer on earth. It is composed of monomers of the sugar glucose that are joined into long chains by covalent beta (1,4) glycosidic linkages that are formed between the $C_1$ aldehyde and $C_4$ hydroxyl groups of the glucose molecule. This chemical structure imparts to cellulose its crystalline, fibrous physical structure. Various forms of cellulose are major industrial agricultural products, particularly cotton and wood. Cellulose is the major component of many products such as paper, textiles, cardboard, construction materials, and many other products. Most cellulose is obtained from the familiar multicellular photosynthetic terrestrial plants. Cellulose is also produced in the oceans by unicellular plankton or algae using the same type of carbon dioxide fixation found in the photosynthesis of land plants.

Certain bacteria can assemble cellulose via non-photosynthetic pathways, requiring glucose, sugar, glycerol, or other organic substrates for conversion into pure cellulose. One such bacterium is *Acetobacter xylinum*, now taxonomically classified as *Gluconacetobacter xylinus*. A single *Acetobacter xylinum* cell can convert up to 108 glucose molecules per hour into cellulose. The *Acetobacter* cells produce sub-microscopic cellulose fibrils which gather in an entangled mesh to produce a gelatinous membrane known as a pellicle. The microbial cellulose so formed benefits from the absence of lignin or hemicelluloses, and is completely biodegradable and recyclable. Microbial cellulose also provides high strength, consistent dimensional stability, high tensile strength, light weight and excellent durability. It is also extremely absorbent in the hydrated state.

Another advantage of microbial cellulose is the potential for direct membrane assembly during biosynthesis. The medium can be suspended in a mold or desired shape to directly form useful products. Extremely thin, sub-micron, optically clear membranes can be assembled. Intermediate steps of paper formation from pulp are unnecessary, and textile assembly from yarn is unnecessary. Cellulose orientation during synthesis is possible for dynamic fiber forming capabilities, and uniaxially strengthened membranes. Crystallization can be delayed by the introduction of dyes into the culture medium, and the physical properties of the cellulose such as molecular weight and crystallinity can be controlled. Also, from this cellulose the direct synthesis of cellulose derivatives such as cellulose acetate, carboxymethylcellulose, methyl cellulose and other derivatives is possible. It is also possible to control the cellulose crystalline allomorph (cellulose I or cellulose II). Brown, Jr., et al., U.S. Pat. No. 4,954,439 disclose a cellulose-producing microorganism which is capable, during fermentation in an aqueous nutrient medium containing assimilable sources of carbon, nitrogen and inorganic substances, of reversal of direction of the cellulose ribbon extrusion such that a cellulose ribbon-bundle having a width of at least two cellulose ribbons is produced.

Microbial cellulose is not intrinsically electrically conductive. Various efforts have been made to impart electrical conductivity to such cellulose, including thermal transformation, deposition of metallic or other conductive particles, and infusion of dyes Yoshino et al. in Synthetic Metals 41-43, 1593-1596 (1991) describe the pyrolyzation of bacterial cellulose at temperatures from 1000 to 3000° C. to transform it to a graphite material. Evans, et al, Pub. No. U.S. 2003/0113610 discloses a method for the deposition of metals onto bacterial cellulose, where the bacterial cellulose matrix is placed in a solution of a metal salt such that the metal salt is reduced to the metallic form precipitates in or on the cellulose matrix.

SUMMARY OF THE INVENTION

An electrically conductive cellulose composite comprises a cellulose matrix, and an electrically conductive carbonaceous material incorporated in the cellulose matrix. The concentration of carbonaceous material is sufficient to provide an electrical conductivity for the composite of at least 10 µS/cm at 25° C. Catalytic metals such as palladium can be subsequently added to the composite by catalytic deposition. The electrical conductivity and structural properties of carbon-cellulose composites according to the invention enable its use in a variety of applications including as a fuel cell electrode in a polyelectrolyte membrane (PEM) fuel cell and as an electrode in a sensor.

BRIEF DESCRIPTION OF THE DRAWINGS

There are shown in the drawings embodiments which are presently preferred, it being understood, however, that the invention is not limited to the precise arrangements and instrumentality shown, wherein.

DETAILED DESCRIPTION OF THE PREFERRED EMBODIMENTS

A cellulose-producing organism is cultured under appropriate conditions to cause the cellulose-producing organism to produce an electrically conductive cellulose composite, or a composite material that upon appropriate heating can be rendered electrically conductive. A carbonaceous material, preferably being an electrically conductive material such as graphite particles, is supplied to the medium, such that the organism will incorporate the electrically conducted carbonaceous material throughout the cellulose matrix of the pellicule. A cleaning procedure can be used to remove the organism, leaving the electrically conductive carbonaceous material entrapped in the composite. The cellulose composite can be dried to a thin membrane, or other desired shape.

The cellulose composite generally includes 10 to 70% w/w carbon/cellulose. The bulk electrical conductivity of the cellulose composite is at least 10 µS/cm at 25° C., such as at least 1 mS/cm, 10 mS/cm, 100 mS/cm, or most preferably at least 1 S/cm at 25 C.

The incorporation of graphite or other carbonaceous materials into the cellulose renders the material electrically conductive. This electrical conductivity has been found to be preserved during subsequent deposition of a catalyst layer, such as palladium, on the surface of the composite. Neither bacterial cellulose without carbonaceous additives nor bacterial cellulose containing only catalysis such as palladium on its surface has been found to be electrically conductive after drying to membranes. Significantly, catalyst comprising cellulose composites according to the invention have been demonstrated to function as a combination electrode/current collector for a fuel cell without the necessity of the insertion of platinum wires for attachment of the multimeter leads as required by earlier related work, as described below.

The catalyst layer can also be deposited by the organism. For example, palladium can be deposited in graphite-containing cellulose by addition of hexachloropalladate solution to a culture of live cellulose producing bacteria that has formed a cellulose pellicule incorporating graphite particles. In this embodiment, the palladium particles are nucleated by reduction of the hexachloropalladate by the cellulose reducing ends, which are aldehyde groups with an $E°$ of about 0.450 V.

Figure 1:
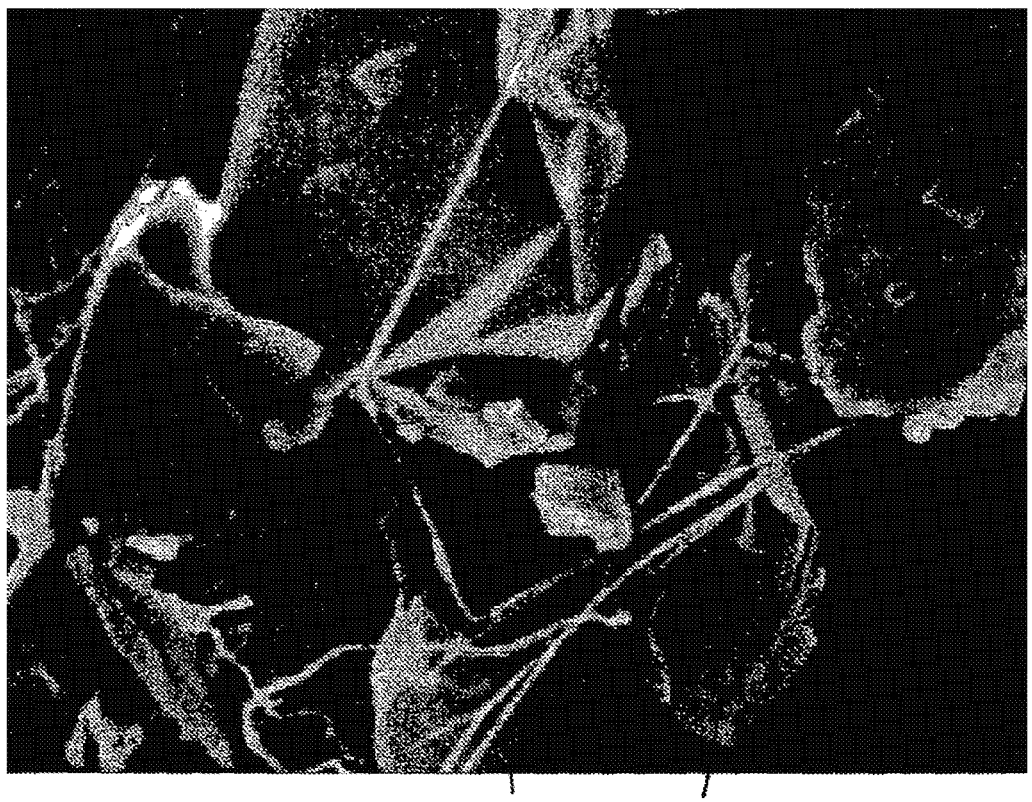
FIG. 1 is a scanned scanning electron microscope (SEM) image of a cellulose composite according to an embodiment of the invention having embedded graphite particles therein.

FIG. 1 is a scanned scanning electron microscope (SEM) image of a cellulose composite according to an embodiment of the invention having embedded graphite particles therein. The graphite particles 105 can be seen to be intermixed with the cellulose fibers 110. It is believed that the bacteria are delivered to extrude their cellulose microfibrils around the graphite particles, entrapping them in a netlike matrix of cellulose. The graphite particles are in sufficiently close proximity to enable electron conduction between the graphite particles, as well as between the graphite and particles of palladium of size about 2-20 nm that can be subsequently formed by catalytic reduction carried out by the cellulose reducing ends as described in Evans, et al, Pub. No. U.S. 2003/0113610. The invention thus provides cellulose composites having an essentially continuous electrically conductive network throughout. Further evidence of the continuous electrically conductive network can be found in the electrical conductivity data presented in the examples below.

The cellulose-producing organism can be any suitable such organism, either now in existence or a new, genetically modified organism. The bacteria should be capable of producing sufficient quantities of cellulose, and must also be capable of incorporating the carbonaceous material into the cellulose matrix. The cellulose-producing microorganism can in one aspect be selected from the genera *Acetobacter* and *Gluconacetobacter*. Species of *Acetobacter* include *Acetobacter aceti, Acetobacter hansenii, Acetobacter xylinum* or *Acetobacter pasteurianus*. Currently preferred organisms include *Gluconoacetobacter hansenii* (ATCC 10821) and *Gluconoacetobacter xylinus*. The taxonomic identification of these bacteria has been described by Yamada et al., (1997), "The phylogeny of acetic acid bacteria based on the partial sequences of 16S ribosomal RNA: the elevation of the subgenus *Gluconoacetobacter* to the generic level", Biosci. Biotechnol. Biochem. 61(8): 1244-1251.

The carbonaceous material can be any material which is or can be made to be electrically conductive and can be incorporated by the organism into the cellulose matrix. The carbonaceous material is generally added in a weight % range of 1 to 5% w/v for addition to the growth medium. The carbonaceous material must have suitable size, composition, and shape in order that the organism can effectively incorporate the material into the cellulose matrix. Graphite powder is one suitable such material. Other suitable carbonaceous materials include activated charcoal, activated carbon, carbon nanotubes, carbon nanofibers, activated carbon fibers, graphite fibers, graphite nanofibers, and carbon black.

The carbonaceous material provided to the organism is preferably electrically conductive. Graphite, powders with particle size of 2-50 microns, for example, have an electrical conductivity at room temperature that has been reported to lie in the range of 10-1000 S cm$^{-1}$ for compacted samples (N. Deprez & D. S. Mc Lachlan, J. Phys. D: Appl. Phys. 21, 101-107, 1988). It is also possible to treat the carbonaceous material so as to make the carbonaceous material electrically conductive or more electrically conductive. Such treatment can occur before or after incorporation of the carbonaceous material into the cellulose matrix by the organism. For example, regarding treatment after incorporation, bacterial cellulose containing incorporated carbonaceous material can be pyrolyzed to a graphite or an electrical conductive amorphous material by heating to temperatures such as 200-1200° C. in a non-oxidizing environment. Similarly, bacterial cellulose into which carbonaceous material is incorporated, followed by deposition of a catalyst such as palladium, nickel, platinum, ruthenium, gold, or silver on the same cellulose matrix, can be pyrolyzed to a graphite or an electrically conductive amorphous material by heating to about 200-1200° C. in a non-oxidizing environment.

The culture medium for the cellulose-producing organism can be optimized for the particular organism that is being cultured. The culture medium should supply the organism with sufficient nutrients such that the cellulose synthesis can take place effectively and efficiently. Synthetic and rich media for the cultivation of Gluconoacetobacter hansenii are shown in Table 1. Other media can be used. The growth of the bacteria can be carried out as described above using Schramm-Hestrin medium with 2% mannitol or fructose substituted for the 2% glucose, using Schramm-Hestrin medium with soy peptone substituted for the bactopeptone, or using a synthetic medium containing 2% glucose, fructose, or mannitol supplemented with niacinamide, thiamine, and calcium pantothenate.

TABLE 1

Two media formulations used by the inventors for production of bacterial cellulose.

| Schramm-Hestrin | Modified Synthetic |
|---|---|
| 2% glucose | 2% glucose |
| 0.5% yeast extract | 0.1% ammonium chloride |
| 0.5% peptone | 0.115% citric acid |
| 0.27% disodium phosphate | 0.33% sodium dihydrogen phosphate |
| 0.115% citric acid | 0.01% potassium chloride |
| | 0.025% magnesium sulfate |
| | 100 mg l$^{-1}$ niacinamide |
| | 100 mg l$^{-1}$ calcium pantothenate |
| | 100 mg l$^{-1}$ thiamine |
| pH 6.2 | pH 6.2 |

The synthetic media formulation was modified from that described in "Biogenesis of Bacterial Cellulose", R. E. Cannon and S. M. Anderson, Microbiology 17(6): 435-447 (1991).
Schramm-Hestrin media was modified from that described in S. Schramm and M. Hestrin, Biochem. J. 57: 345-352 (1954), "Synthesis of Cellulose by *Acetobacter xylinum*. 2. Preparation of freeze-dried cells capable of polymerizing glucose to cellulose."

The vitamins niacinamide, calcium pantothenate, and thiamine are prepared as a 1000× stock solution, filter-sterilized, and added to the autoclaved media after it is cooled to room temperature. Without adjustment, the pH is about 6.4. The bacteria are cultured under temperature and pH conditions which are suitable to facilitate the cellulose synthesis and incorporation of the carbonaceous material. As the bacteria synthesize the cellulose on the top of the liquid media, the graphite or other carbon particles are added after an initial cellulose layer has been synthesized during the incorporation under these static culture conditions due to the effects of gravity on the graphite particles causing them to fall to the bottom of the culture dish.

As noted above, electrically conductive cellulose compositions according to the invention can be used to form a number of different products. These products include membranes of various thickness and dimensions. The compositions can be combined with other materials to alter the properties of the final product. For example, a layer of metal can be disposed on and in contact with the cellulose composites of the invention. Such metal deposition techniques are known in the art, and can include those shown in Pub. No. US 2003/013610, the disclosure which is incorporated by reference. The incorporated metal can be suitable a metal, such as the catalyst, Pd, Pt, Ru, Au or Ni. Other materials can be incorporated into or on the cellulose composite.

Figure 2:
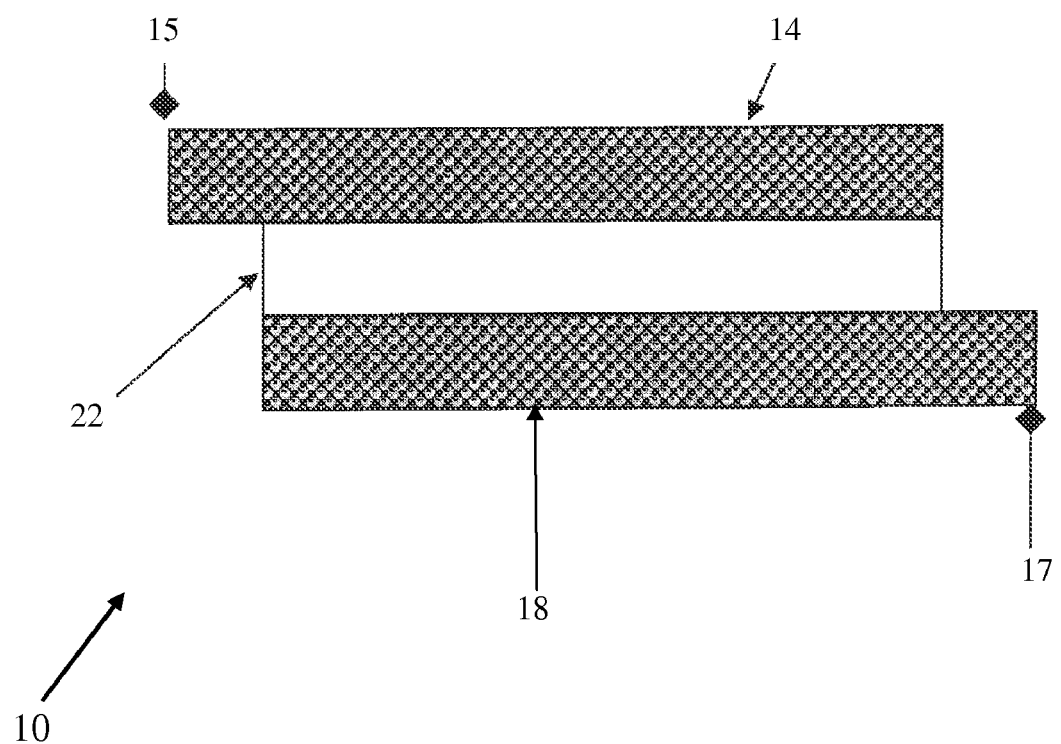
FIG. 2 is a schematic diagram depicting a membrane electrode assembly (MEA) according to the invention.

For example, the catalyst-containing cellulose composite can be used to form membrane electrode assemblies (MEA) for use in fuel cells. There is shown in FIG. 2 a MEA 10 having electrodes (anode, cathode) 14,18. The electrodes 14,18 are formed from electrically conductive cellulose compositions of the invention, with catalyst particles (now shown) formed within the cellulose matrix, such as palladium particles. Although not shown in FIG. 2, the catalyst particles can be a discrete layer coating one side of the electrodes 14, 18, as is observed with vapor deposition or with electroplating. A proton exchange membrane (PEM) 22 is disposed between the catalyst comprising electrodes 14,18. The PEM 22 can be any suitable material, and can comprise cellulose. MEA 10 also includes anode lead 15 for connection to anode 14 and cathode lead 17 for connection to cathode 18. Electrically conductive cellulose membranes according to the invention can also be used in the assembly of membrane electrode assemblies for use in electronic devices, fuel cells and biosensors.

EXAMPLES

The present invention is further illustrated by the following specific Examples, which should not be construed as limiting the scope or content of the invention in any way.

The formation of electrically conductive cellulose composites according to the invention is illustrated by the following example. *Gluconoacetobacter hansenii* (ATCC 10821) is cultivated in Schramm-Hestrin medium (2% glucose, 0.5% bactopeptone, 0.5% yeast extract, 0.27% disodium monohydrogen phosphate, 0.115% citric acid, pH 6.2) under static conditions in shallow culture dishes at 23-28° C. Typically, 10 ml of inoculated culture medium are placed in a 6-cm culture dish or 20 ml in a 10 cm culture dish. After the bacteria have started to form a clear, gel-like cellulose pellicule, usually about 3 days, 0.5 g sterilized graphite (Alfa Aesar, Ward Hill, Mass., electronic grade, 2-15 microns in size) is suspended as a slurry in culture medium, then added to the bacterial culture on top of the cellulose layer. Incubation is continued until the graphite particles have become entrapped in the growing cellulose, about 5-10 days.

The cellulose pellicule is then harvested by removal from the culture dish to a heat-resistant container for cleaning to remove the organism and media components. The cellulose is first heated in distilled water to 90-100° C. for 1-2 h, then washed with 3 changes of distilled water. It is then incubated in 1% sodium hydroxide solution for 1-3 days. The sodium hydroxide is then neutralized by the addition of 1.5 volumes of 0.5 M sodium acetate buffer, pH 4.5. Acetate is removed by soaking the cellulose in distilled water. The cellulose is then stored in 20% ethanol or isopropanol. Other cleaning routines can be employed, such as heating the harvested cellulose in distilled water in an autoclave, and utilization of other alkali solutions such as Trizma base and ammonium hydroxide, and other acids for neutralization such as hydrochloric acid and phosphoric acid. When activated charcoal (medium grade) is substituted for the graphite in the procedure described above, it is incorporated into the cellulose pellicule by the bacteria in a similar manner to that observed for the graphite particles.

The cellulose pellicule containing graphite incorporated in vivo is incubated in a solution of hexachloropalladate for preparation of a cellulose/graphite/palladium membrane according to the invention. The resistance of the oven-dried pellicules was measured using a Wiley 200 Multimeter equipped with standard copper leads at each electrode. As expected, the electrical resistance was lower (electrical conductivity higher) for the cellulose containing graphite than that of the cellulose containing activated charcoal. Infinity (∞) represents an electrical resistivity too high to measure and µS=microSiemens.

TABLE 2

Electrical Conductivity of Graphite-Cellulose Membranes

| Sample Measured | Electrode Separation (cm) | Resistivity [Mohm] | Conductivity [µS/cm] |
|---|---|---|---|
| Bacterial Cellulose no additives | 10 | ∞ | 0 |
| Activated Charcoal Bacterial Cellulose | 5 | 0.10 | 10 |
| Activated Charcoal Bacterial Cellulose Palladium (one palladization incubation) | 2 | ∞ | 0 |
| Activated Charcoal Bacterial Cellulose 2Palladium (two palladization incubations) | 2 | ∞ | 0 |
| Bacterial Cellulose Palladium | 6 | ∞ | 0 |
| Bacterial Cellulose Palladium | 6 | ∞ | 0 |
| Graphite Bacterial Cellulose | 10 | 0.0030 | 33.3 |
| Graphite Bacterial Cellulose | 10 | 0.0024 | 41.6 |
| Graphite Cellulose Palladium | 6 | 0.0011 | 151.5 |

Figure 3:
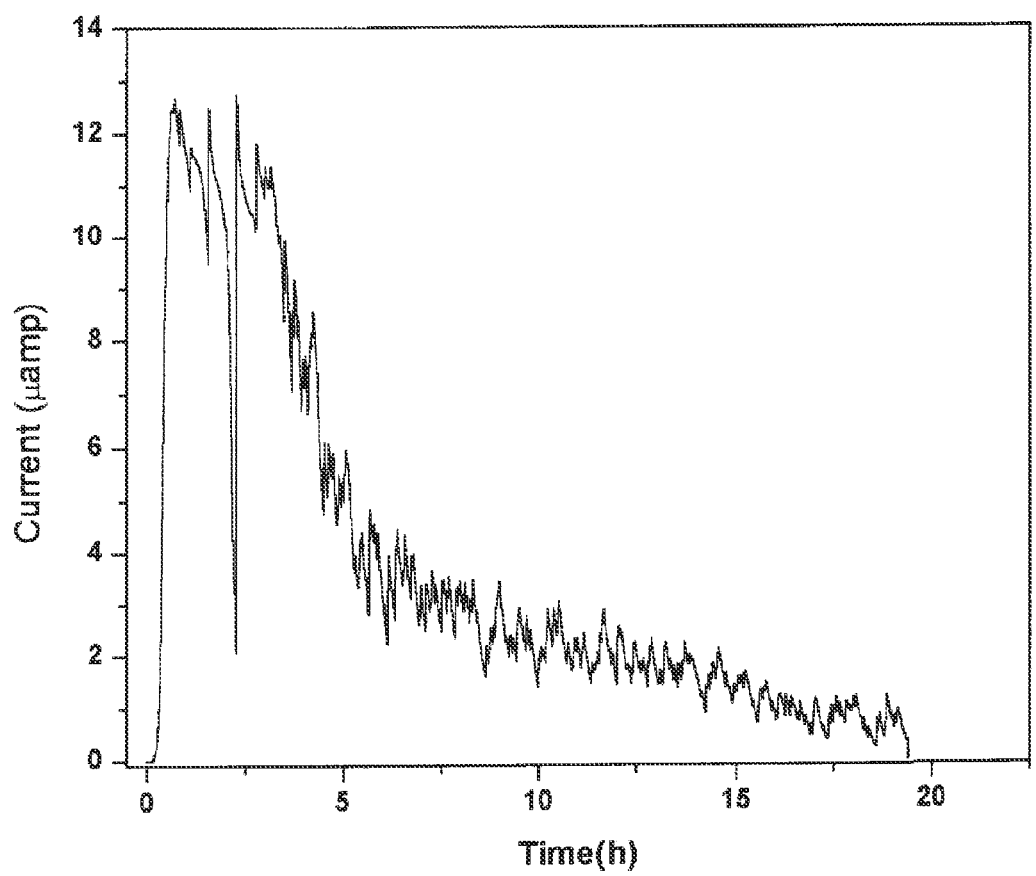
FIG. 3 is a graph depicting current production from a proton exchange membrane (PEM) fuel cell formed from a MEA based on electrically conductive cellulose composites according to the invention.

A fuel cell was assembled using electrodes comprising Pd coated cellulose-graphite composite according to the invention. The proton conducting membrane layer was a bacterial graphite/cellulose pellicule that had been soaked in a 1 M potassium chloride solution. The palladium-graphite electrode layers were used as the electrode, current collector and catalyst. The layers were assembled by sequential drawing on a standard dryer with heating to 60° C. for 10 minutes. The tested fuel cell assembly had final dimensions of 2 cm×2 cm×1 mm. The fuel cell assembly was tested by placing it between rubber O-ring seals connecting a glass container containing 3 ml of 10% acetic acid in water and 180 mg of iron powder and an open glass tube. The acetic acid and iron filings generate $H_2$ by the acid displacement reaction. The open tube allows free diffusion of $O_2$ from the atmosphere to the anodic side of the fuel cell. This testing apparatus was described previously in Evans, et al, Pub. No. U.S. 2003/0113610. The current output for a single palladium-graphite cellulose fuel cell formed as described above is shown in FIG. 3.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A method of forming electrically conductive cellulose composites, comprising the steps of:
   providing a cellulose-producing bacterium in cultivated conditions including a suitable culture medium, and
   adding electrically conductive carbonaceous material to said culture medium at a point at which the bacterium has initiated cellulose production to form a cellulose matrix comprising a plurality of fibers, wherein said bacterium incorporates said electrically conductive carbonaceous material in said cellulose matrix produced to provide an electrically conductive cellulose composite comprising the cellulose matrix and the electrically conductive carbonaceous material, wherein a concentration of said electrically conductive carbonaceous material is sufficient to provide an electrical conductivity for said composite of at least 10 µS/cm at 25° C.

2. The method of claim 1, wherein said carbonaceous material is at least one selected from the group consisting of activated charcoal, activated carbon, graphite, carbon nanotubes, activated carbon fibers, graphite fibers, carbon nanofibers, graphite nanofibers and carbon black.

3. The method of claim 1, wherein a weight percentage range for said carbonaceous material is 1-5% w/v for addition to said culture medium.

4. The method of claim 3, wherein said electrically conductive cellulose composite contains 10 to 70% w/w carbon/cellulose.

5. The method of claim 1, wherein said bacterium is of the genus *Gluconoacetobacter* or *Acetobacter*.

6. The method of claim 1, further comprising the step of adding a metal solution to said culture medium, wherein metal particles are formed within said cellulose matrix.

7. The method of claim 6, wherein said metal solution comprises Pd, Pt, Ru, Au, or Ni.

* * * * *